United States Patent
Greaves et al.

(10) Patent No.: US 9,745,242 B1
(45) Date of Patent: Aug. 29, 2017

(54) METHOD FOR PRODUCTION OF THYMOQUINONE

(71) Applicant: Kemin Industries, Inc., Des Moines, IA (US)

(72) Inventors: John A. Greaves, Ankeny, IA (US); Brindha Narasimhamoorthy, West Des Moines, IA (US); Vandana Srivastava, Johnston, IA (US); Norman Cloud, Ames, IA (US); Dawn Clark, Urbandale, IA (US)

(73) Assignee: KEMIN INDUSTRIES, INC., Des Moines, IA (US)

( * ) Notice: Subject to any disclaimer, the term of this patent is extended or adjusted under 35 U.S.C. 154(b) by 0 days.

(21) Appl. No.: 15/348,322

(22) Filed: Nov. 10, 2016

(51) Int. Cl.
*C07C 46/00* (2006.01)
*A01G 1/00* (2006.01)
*C07C 46/10* (2006.01)
*A01G 25/00* (2006.01)

(52) U.S. Cl.
CPC .............. *C07C 46/10* (2013.01); *A01G 1/001* (2013.01); *A01G 25/00* (2013.01)

(58) Field of Classification Search
CPC .......... C07C 46/00; C07C 46/10; A01G 1/001
See application file for complete search history.

(56) References Cited

U.S. PATENT DOCUMENTS

| | | | |
|---|---|---|---|
| 9,029,610 B2 * | 5/2015 | Rohlfsen | A01G 1/001 568/756 |
| 9,073,824 B2 * | 7/2015 | Rohlfsen | A01G 1/001 |
| 9,180,155 B2 * | 11/2015 | Babish | A61K 36/71 |

* cited by examiner

*Primary Examiner* — Sikarl Witherspoon
(74) *Attorney, Agent, or Firm* — Nyemaster Goode P.C.

(57) ABSTRACT

A method of producing thymoquinone and/or thymohydroquinone in *Monarda* by growing *Monarda* with elevated levels of carvacrol and/or thymol in the fresh plant tissue and vigorous growth, harvesting the *Monarda*, leaving the *Monarda* to senensce in the presence of oxygen and extracting the thymoquinone and/or thymohydroquinone from the senesced tissue.

6 Claims, 9 Drawing Sheets

METHOD FOR PRODUCTION OF THYMOQUINONE

FIELD OF THE INVENTION

The present invention relates generally to a method for production of thymoquinone and, more specifically to a novel method of growing plants that produce carvacrol and/or thymol, including *Monarda fistulosa*, for the efficient harvest of thymoquinone essential oil.

BACKGROUND OF THE INVENTION

*Monarda fistulosa* (sometimes also known as horsemint, Oswego tea, bergamot or bee balm) is a member of the Lamiaceae (Mint) family. It is a native mid-western prairie perennial plant species which propagates via slender rhizomes and via seed. It can be vegetatively propagated via rooted cuttings to generate clonal lines from a single plant. When the term "*Monarda*" is used herein it is understood that it includes plants known by these names, as well, provided the plant meets the characteristics of the *Monarda* genus.

*Monarda fistulosa* is common to roadsides, meadows, native prairie conservation sites and woodland borders, and was highly prized by native Americans and later pioneer settlers for its medicinal properties.

*Monarda fistulosa* was introduced into the *Materia Medica* in the 1850s due to its medicinal properties. Leaves, stems and flowers are all used medicinally with greater than 17 bioactive molecules identified, including thymol and carvacrol. Author Michael Wood (in his book *Herbal Wisdom*) describes this species by one of its indigenous names "sweet leaf" as one of the most valuable plants in his herbal cupboard.

*Monarda fistulosa* is very similar to oregano (*Origanum vulgare*) and thyme (*Thymus vulgaris*) in its ability to accumulate thymol and carvacrol in its leaves and other plant parts. *Monarda fistulosa* has been known to produce thymoquinone since at least as early as 1907 (Wakeman, *Pigments of Flowering Plants*, Transactions of the Wisconsin Academy of Science, Arts and Letters, Volume 19, pp 785-795 (1907)).

What was not previously known was that during senescence of leaves or flowers, carvacrol and thymol are converted to thymoquinone (TQ) which therefore accumulates in dead or dying tissue. Thymoquinone does not accumulate to any degree in fresh tissue. Genetic variation exists for the accumulation of (conversion from carvacrol and thymol) thymoquinone in dead, dying or post-harvest tissue just as it does for the accumulation of carvacrol and thymol in healthy fresh tissue. Accordingly, any person skilled in the art of plant breeding can select plants that accumulate high levels of carvacrol or thymol (or thymoquinone from senescent tissue) from a segregating population of plants in order to optimize accumulation levels.

Several hundred seed can be planted and grown under a uniform controlled or field environment and once the plants are in full vegetative stage, leaf tissue can be taken for phytochemical analysis of carvacrol and thymol. Day length needs to be greater 12 hours with light intensity similar to full sunlight as accumulation is day length and light intensity driven. Individual plants within a population (clonal lines) that accumulate extreme levels of carvacrol and thymol (>3% on a dry matter basis) can be selected and propagated (scaled) either vegetatively or by seed similar to other crops. Populations of plants of *Monarda fistulosa* can be improved for accumulation of carvacrol and thymol using a well-known breeding technique of mass selection, resulting in seeded varieties that hyper-accumulate these molecules.

Any person skilled in the art of agronomy and field crop production can grow a crop of improved *Monarda fistulosa*, selected for higher accumulation of carvacrol or thymol in large acreages in order to generate biomass for harvest and extraction using well known and frequently practiced agronomic methods.

An early example of a method for commercial production of thymol from a closely related species (*Monarda punctata*) was described in 1916 in USDA Bulletin 372 by S. C. Hood.

Planting density can be optimized to (a) reduce weed pressure; and (b) optimize biomass accumulation per unit area. The United States Department of Agriculture Natural Resources Conservation Division recommends a planting density for *Monarda fistulosa* of 3.6 lbs per acre. Further, in a study published in 1916, it was recommended that the planting density be such that the usual cultivation methodologies result in plants that shade the ground and thus prevent the growth of weeds (1916 in USDA Bulletin 372, ibid.).

Those skilled in the art of steam distillation can generate essential oil of *Monarda fistulosa* which is high in carvacrol or thymol from freshly harvested biomass; or with increasing levels of thymoquinone from senescing or senescent biomass. Steam distillation followed by subsequent decanting of the oil is a frequently practiced process for generating essential oil. Carvacrol and thymol oils are generated from oregano using this method.

Unique, hyper-accumulating clonal lines for carvacrol and/or thymol of *Monarda fistulosa* represent optimum assemblages of alleles derived through breeding and selection.

Wild Bergamot (*Monarda fistulosa* L.) is a native Iowa wildflower species in the mint (Lamiaceae) family, and is a potential source of thymoquinone. Thymoquinone is a molecule of interest for use as a functional molecule for dandruff control in shampoos and other personal care products. Thymoquinone is known for its anti-inflammatory, antimicrobial, antioxidant and immunomodulatory effects and is used for treating skin rashes, insect bites, and sun burns. It has also been shown to have significant anti-cancer activity carvacrol and its geometrical isomer thymol can be oxidized to thymoquinone, which has a potential commercial value considerably higher than its precursor's thymol and carvacrol (FIG. 1). The essential oils derived from plant species such as oregano are dominated by carvacrol and thymol while essential oils from wild bergamot and *Nigella sativa* are dominated by thymoquinone which occurs less frequently in nature.

Development of proprietary *Monarda* clonal lines with high levels of thymoquinone (thymoquinone levels ≥2.5%) combined with high biomass will result in an economically viable source of thymoquinone.

In addition to inherent genetic variation, the accumulation of these molecules is influenced by physiological maturity of the plants and the environmental conditions in which they are grown. The composition and quantity of the essential oils in several Lamiaceae species are known to change with physiological maturity and environmental conditions such as day length and light intensity. Little research has been done in understanding the variation for thymoquinone content among *Monarda* collections; nor time of harvest for maximizing thymoquinone content in the essential oils. The highest level of thymoquinone reported in a *Monarda* collection was 0.36% on a dry matter basis in flowers and 0.26% in leaves and stems. The amounts of carvacrol, thymol and other phenolic compounds differ relative to physiological maturity of the plants and flowers and therefore, distillation of flower heads harvested at different maturity stage may result in oil having different profiles.

Another study completed in 1993 looked at *Monarda* as a source of certain oils, specifically, geraniol, linalool, thymol and carvacrol. This study also presented the idea that plants of a given species but grown and maintained in different geographical regions may yield different oils. (Mazza, G., F. A. Kiehn, and H. H. Marshall, 1993, *Monarda*: A source of geraniol, linalool, thymol and carvacrol-rich essential oils, p. 628-631. In: J. Janick and J. E. Simon (eds.), New crops, Wiley, New York.)

It is well known that planting density can affect the oil yield and composition in plants. For example, in dill (*Anethum graveolens* L.), increasing plant density increased the amount of phellandrene, α-pinene and dill ether (Callan, N. W. et al. *Industrial Crops and Products* 25 (2007) 282-287). The oil yield of parsley (*Petroselinum crispum*) was found to be increased when the plant density of either flat-leafed or curly-leafed parsley was increased (Petropoulos, S. A. et al. *Scientia Horticulturae* 115 (2008) 393-397). Similarly, increasing plant density increased the essential oil production in German chamomile (*Matricaria chamomilla* L.) (Pirzad, A. et al. *Australian Journal of Agricultural Engineering* 2(5) (2011) 120-126).

Given that agronomic methods for efficiently growing *Monarda fistulosa* on a commercial scale and collecting the essential oils containing carvacrol and/or thymol are well within the skill in the art, what is needed are varieties of *Monarda fistulosa* that hyper-accumulate carvacrol and or thymol and a method of converting such compounds efficiently into thymoquinone and/or thymohydroquinone.

SUMMARY OF THE INVENTION

The present invention includes a method of producing thymoquinone and/or thymohydroquinone from *Monarda fistulosa*, including varieties that hyper-accumulate carvacrol and/or thymol and therefore, upon senescence, yields high levels of thymoquinone and/or thymohydroquinone. The preferred varieties also have good agronomic characteristics that result in a high amount of biomass for harvest and extraction of the desired compounds.

It was therefore one objective of the present invention to grow varieties of *Monarda fistulosa* that hyper-accumulate carvacrol and/or thymol and employ a novel method of converting such compounds efficiently into thymoquinone and/or thymohydroquinone.

It was another objective of the present invention to grow varieties of *Monarda fistulosa* that, in addition to hyper-accumulating carvacrol and/or thymol for conversion into thymoquinone and/or thymohydroquinone, have good agronomic characteristics so as to produce a high level of biomass from which the desired compounds may be collected.

It was a further objective of the present invention to provide novel varieties of *Monarda fistulosa* that provide an economically viable manner of producing thymoquinone and/or thymohydroquinone.

An object of the present invention is to grow and use a specialized method of harvest of varieties of *Monarda* with a high level of carvacrol and/or thymol, and therefore, with proper treatment, thymoquinone and/or thymohydroquinone, for use as a bioactive molecule in human and animal food, beverages and personal care products.

Another object of the invention is the growth and specialized harvest of varieties of *Monarda fistulosa* that are novel, stable, and uniform and have good agronomic characteristics that permit efficient cultivation of the variety as a crop that produces a high amount of biomass from which the afore-mentioned bioactive molecules can be extracted.

It has been known that planting rates for *Monarda fistulosa* are recommended to be at least 3.6 lbs./acre. Such planting densities result in a crop that has sufficient plant density to shade the ground and thus prevent the growth of weeds.

Further, it was recommended as far back as at least 1916 that covering seed with soil and keeping it moist after seeding increases germination (1916 in USDA Bulletin 372, ibid.). It is, of course, well known that rolling the soil with a roller provides compression and a better barrier for retaining moisture and for protection against birds or other pests while the seeds germinate.

Consistent with the known literature, the present invention recommends planting rates ranging around 3.6 lbs/acre either via broadcast seeding or drilling. The method advocates certain practices related to harvesting *Monarda fistulosa* for best yield of the desired compounds, and in particular, thymoquinone, and describes means and method for separating the thymoquinone from the plant.

Other objects, features, and advantages of the present invention will be readily appreciated from the following description. The description makes reference to the accompanying drawings, which are provided for illustration of the preferred embodiment. However, such embodiment does not represent the full scope of the invention. The subject matter which the inventor does regard as his invention is particularly pointed out and distinctly claimed in the claims at the conclusion of this specification.

DETAILED DESCRIPTION OF PREFERRED EMBODIMENTS

Figure 1:
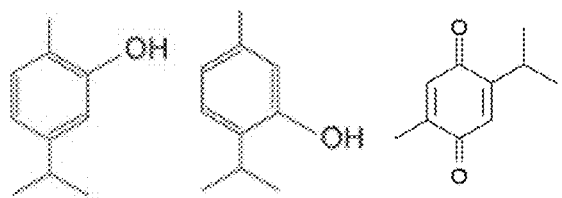
FIG. 1 is a drawing of the structures of carvacrol (left); thymol (middle) and thymoquinone (right).

In the present invention, *Monarda* plants are grown until carvacrol and/or thymol is/are present in plant tissues or plant material. The plants are cut and the cut material is allowed to senesce either with or without the purposeful application of water. The period of senescence is over a period of at least one day and up to about 14 days, including 2, 3, 4, 5, 6, 7, 8, 9, 10, 11, 12 and 13 days. The purposeful application of water is done at least once over the period, and may be done multiple times, for example once a day, once every other day, once every third day, and so on. Purposeful application of water may be done by any known method, such as hand watering or mechanical watering, using a sprayer or irrigation methodologies.

In the present invention, the step of extended senescence, with or without the purposeful application of water, will enhance the conversion of carvacrol and/or thymol into thymoquinone up to a range of levels of between 10 w/w % and 40 w/w % of the oil distilled from the plant material, and all values within that range. Stated another way, in preferred embodiments of the invention, the range of thymoquinone in the oil can take any value "ab.cd" ppm wherein a is selected from the numerals 1, 2, 3 and 4, and b, c and d are selected from the numerals 0, 1, 2, 3, 4, 5, 6, 7, 8 and 9 except b, c and d are all 0 when a is 4.

Example 1—Development of Hyper-Accumulating *Monarda fistulosa* Clonal Lines Seed of *Monarda fistulosa* was obtained from a commercial seed supplier in the USA. Approximately 400 genetically distinct plants were generated from this seed source. The plants were transplanted from the greenhouse to a small field plot during May, 2013. The plants were allowed to grow and develop through the initial summer season of 2013 (Year 1) and were then over-wintered in this field plot.

Most of the plants emerged early in the next year (Year 2) and grew rapidly through the early spring months. A total of 200 plants from this population were randomly tagged for tissue analysis. Leaf tissue samples were taken on Jun. 14, 2014. Leaf tissue samples were air dried for approximately 4 weeks in indirect sunlight prior to analysis. A rapid micro-extraction and quantitation method was developed and used to measure genetic variation for carvacrol, thymol and thymoquinone.

All 200 samples were analyzed and showed a large genetic variation for all three molecules. Out of 200 plants tested, the range in thymoquinone was 0.51% to 2.46% on a dry matter basis with 18 plants with >2.0% thymoquinone on a dry matter basis. The range of accumulation of thymoquinone was from the highest at a level of 2.46% on a dry matter basis, relative to the lowest thymoquinone accumulation of 0.51%.

At this time, thymoquinone accumulation occurred in was thought to occur in fresh leaf tissue (fixed during drying) and that we had been able to identify several hyper-thymoquinone accumulating plants.

The tissue was sampled again on Jul. 23, 2014, and instead of allowing the samples to air dry for four weeks, the samples were freeze dried and sent for analysis. To our surprise, no thymoquinone was found in these samples and it was hypothesized that there was only a narrow window for thymoquinone accumulation in *Monarda*. The dates in between which the data had been obtained was carefully noted. The population was once again allowed to grow to maturity and flower followed by overwintering into the next year (Year 3).

Beginning in April 2015 (Year 3), monthly samples of leaf tissue were taken from the 18 hyper-thymoquinone accumulating plants (identified in Year 2) expecting thymoquinone accumulation to begin as day length and light intensity increased through spring into summer. Leaf tissue samples were continued to be taken through the end of June, but unexpectedly no accumulation of thymoquinone was found in any of these plants that had shown a high-thymoquinone phenotype the previous year.

Figure 2A:
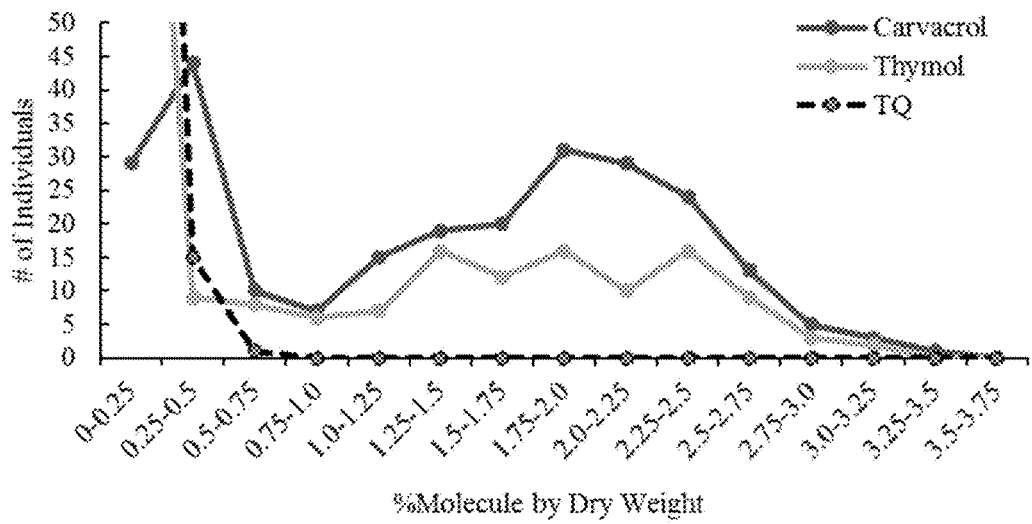
FIG. 2A is a graph showing population frequency distribution for carvacrol, thymol and thymoquinone (TQ) in freeze-dried tissue.
Figure 2B:
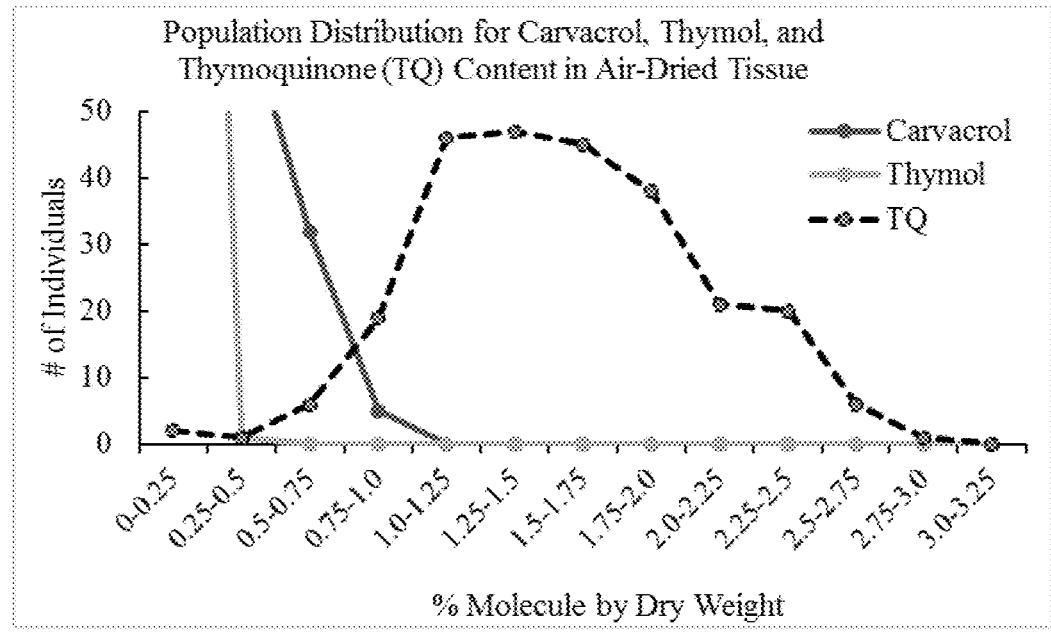
FIG. 2B is a graph showing population frequency distribution for carvacrol, thymol and thymoquinone (TQ) in air-dried tissue.

The analytical procedure used by the biochemical screening lab was checked and they found no problems. Towards the end of June, the lab picked up an anomaly from one sample which from the Year 3 data set showed thymoquinone accumulation of 1.8% on a dry matter basis. This was the only plant in the original 18 selections that showed any thymoquinone accumulation. On closer inspection, this plant sample had been mistakenly left in the field for over a week before being found and sent to the lab. Leaf tissue samples were then taken from all 18 selections plus the whole population and the samples were split from each plant to be either (a) freeze dried for 48 hours; or (b) air dried for 3-4 weeks. Freeze-dried samples showed elevated levels of carvacrol and thymol but no thymoquinone. Only in the air dried samples was thymoquinone detected and ranged from 1.0% to 2.79% on a dry matter basis (FIG. 2A and FIG. 2B).

The same experiment was conducted for all 200 plants within the population and a separation in data sets for thymoquinone accumulation between freeze-dried tissue and prolonged air-dried tissue from the same plants was observed. This experiment showed that thymoquinone does not accumulate per se in fresh, healthy tissue; but does accumulate when tissue from the same plant is allowed to dry (forced senescence) for up to 4 weeks. Thymoquinone must therefore be a breakdown or oxidation product of carvacrol or thymol in post-harvest tissue.

It is likely that thymoquinone levels can be optimized further by optimizing timing of harvest relative to pre-harvest accumulation of carvacrol and thymol.

The essential oil and their contents were found to be at the highest during the pre-flowering stage. None of the plants were flowering at the time of harvest during the first week of June and yet the carvacrol and thymol content were found to be at the maximum levels. Hence *Monarda* should be harvested pre-flowering in order to maximize the carvacrol and thymol yield. Under suitable growing conditions, with adequate rainfall, these plants could be harvested twice during the growing season; once during mid June and again during the last week of August.

The present invention includes planting seed of *Monarda fistulosa* or any of the species of *Monarda* in a field at a rate between about 2.5 lbs per acre and about 5 lbs per acre and more preferably between about 3.6 lbs per acre, mowing the field regularly the first year, and then harvesting it in years thereafter. The lifetime of plants for a single planting is typically 5-7 harvests, but may be longer or shorter depending on soil conditions, climate and husbandry practices. The equipment used to condition the field, plant the seed, mow the plants, cut the plants, and gather the plants may each be of any type readily known and understood by one of skill in the art.

During the first season, the field may be mowed on a regular basis. Depending on rainfall, soil and climate conditions, mowing may be done as often as 4-6 times in a season or as infrequently as 2-4 times. Mowing frequency is dictated by the height of the plants. Mowing is aimed to keep the weed height reduced to allow the *Monarda* to become established. The planting rate, the growth rate, the size of the plants, and the *Monarda*'s own chemical defenses result in a crop that typically requires no further herbicide treatments but for, perhaps, an occasional weed patch which may be controlled via hand sprayer or physical removal.

In midsummer, *Monarda fistulosa* plants produce a lavender colored fragrant flower. The plants are harvested prior to flower peak which, in the Midwest United States, is generally mid June. Harvest of *Monarda fistulosa* fields cultivated in the manner of the present invention may be accomplished in several ways using various equipment. A preferred method is to employ is a plant cutting machine with a cutter bar to cut the plants and leave them lay where they were cut. Pending U.S. patent application Ser. No. 13/359,045, filed Jan. 26, 2012, recites: "The cut plants should remain in the field for 2-8 hours, preferably 2-6 hours and more preferably 4-6 hours. It is best, but not critical, that these days be warm and sunny. Leaving the plants lay causes the carvacrol and thymol in the plants to oxidize into thymoquinone (FIG. 1). The cut plants are then gathered by a suitable device such as a forage chopper 18 and placed in means to transport 30 them from the field."

Pending U.S. patent application Ser. No. 13/804,026, filed Mar. 14, 2013, recites: "The method of cultivation just described increases germination, decreases herbicide use and fuel use, and increases the yield of *Monarda fistulosa* oil specifically carvacrol, thymol, and thymoquinone (TQ) and thymohydroquinone (THQ). The thymoquinone and thymohydroquinone levels, together, constitute about 5% of the oil distilled." The present invention shows up to 27.5% without purposeful watering (Table 1 of Example 2) and up to 40% with purposeful watering.

In one embodiment, means to transport the cut and senesced plants comprises what is well known in the art as a steam distillation wagon such as is widely used as one of several methods for removing oil from plants of the Lamiacea family, including *Monarda fistulosa*.

The above-mentioned cultivation method results in oil content that is commercially desirable, namely, increased amounts of carvacrol, thymol, thymoquinone, and thymohydroquinone of high quality. Known recommended planting rates for *Monarda fistulosa* include planting rates of 3.6 lbs. per acre, exactly the rates to provide the better means for cultivating and harvesting the plants and obtaining the desired essential oils they contained at the level of oil quality desired. Oil quality at such known planting rates is high at least partially due to the reduction and near elimination of weed pressure and its resulting contamination. The quality may also be partially attributed to low uses of herbicides or pesticides.

Example 2—Oxidative Bioconversion of Thymol and Carvacrol to Thymoquinone in Selected Lines of *Monarda fistulosa* L During winter months of 2014 and 2015, 31 clonal lines of *Monarda fistulosa* were propagated and planted at greenhouses in Iowa. Propagates were planted in 31 small plots alongside a previously established 5 acre *M. fistulosa* plot. This 5 acre plot was grown from a seed source obtained from a commercial seed supplier.

Plants in each of these plots were allowed to grow and develop through the 2015 summer season and were then over-wintered in this field plot. Most of the plants emerged in early 2016 and grew rapidly through the early spring months.

Another study was conducted in 2016 to characterize and compare the content of thymoquinone, thymol, and carvacrol in the essential oil from a subset of 31 selected lines of *Monarda fistulosa* before and after two weeks of post-harvest drying. The unselected population of *Monarda fistulosa* grown in the 5 acre plot was used as a control. The leaf tissue (top 8") was harvested from the selected clonal lines plot and the unselected plot in on May 26 and 27, 2016. Biomass collected from each plot was divided into two halves. One half of the biomass was wilted for 24 hours and steam distilled to obtain essential oil. Second half of the sample was wilted under shade for 14 days and steam distilled to obtain essential oil.

The oil was analyzed using HPLC to quantitate carvacrol, thymol and thymoquinone in triplicates (Table 1).

TABLE 1

Carvacrol, thymol and TQ content in their essential oils in selected *M. fistulosa* clonal lines

| | TQ % | | Carvacrol % | | Thymol % | |
| --- | --- | --- | --- | --- | --- | --- |
| | Day 1 | Day 14 | Day 1 | Day 14 | Day 1 | Day 14 |
| KI-Mf0131 | ND | 20.35 ± 1.07 | ND | ND | 57.95 ± 3.40 | ND |
| KI-Mf0397 | ND | 18.26 ± 0.90 | ND | ND | 40.80 ± 2.21 | ND |
| KI-Mf0399 | ND | 19.54 ± 1.18 | ND | ND | 56.53 ± 1.12 | ND |
| KI-Mf0424 | ND | 19.80 ± 0.63 | ND | ND | 71.93 ± 3.46 | 8.69 ± 0.16 |
| KI-Mf0462 | ND | 26.79 ± 1.64 | ND | ND | 49.21 ± 0.47 | ND |
| KI-Mf0785 | ND | 25.55 ± 0.14 | 4.71 ± 0.17 | ND | 68.47 ± 1.94 | 9.41 ± 0.05 |

TABLE 1-continued

Carvacrol, thymol and TQ content in their essential oils in selected *M. fistulosa* clonal lines

| | TQ % | | Carvacrol % | | Thymol % | |
|---|---|---|---|---|---|---|
| | Day 1 | Day 14 | Day 1 | Day 14 | Day 1 | Day 14 |
| KI-Mf0606 | ND | 17.09 ± 0.45 | ND | ND | 51.39 ± 1.70 | ND |
| KI-Mf0803 | ND | 22.43 ± 1.87 | 3.60 ± 0.16 | ND | 55.00 ± 2.53 | ND |
| KI-Mf0786 | ND | 27.5 ± 1.73 | 3.2 ± 0.65 | ND | 55.7 ± 0.97 | ND |
| KI-Mf0648 | ND | 22.7 ± 1.27 | ND | ND | 37.6 ± 2.06 | 17.3 ± 0.22 |
| KI-Mf1054 | ND | 21.73 ± 2.55 | ND | ND | 43.37 ± 3.77 | ND |
| KI-Mf1056 | ND | 20.55 ± 2.17 | 4.04 ± 0.03 | ND | 61.21 ± 1.32 | ND |
| KI-Mf0571 | ND | 25.24 ± 3.47 | 92.72 ± 1.67 | 51.21 ± 2.62 | 4.07 ± 0.08 | ND |
| KI-Mf0552 | ND | 25.99 ± 2.86 | 96.7 ± 0.81 | 59.64 ± 1.62 | ND | ND |
| KI-Mf0734 | ND | 15.68 ± 0.49 | 41.47 ± 3.78 | 7.70 ± 0.05 | ND | ND |
| KI-Mf0661 | ND | 16.56 ± 0.08 | 51.68 ± 1.27 | 11.95 ± 0.12 | ND | ND |
| Unselected material | ND | 5% | 28% | ND | 15% | ND |

ND - represents not detected;

Clonal lines selected for high thymol showed 40 to 72% thymol by weight before extended drying and showed a conversion of up to 100% to an average yield of 21% Thymoquinone on a weight basis. The lines selected for high carvacrol ranged between 90 to 92% carvacrol by weight before drying and showed a conversion of less than 30% to an average yield of 25% thymoquinone. The unselected material generated 28% carvacrol and 15% thymol before drying that converted to less than 5% thymoquinone after drying. The conversion of thymol and carvacrol in this mixed population was close to 70%.

Example 3—Method of Increasing the Bioconversion of Carvacrol and Thymol to Thymoquinone by Purposeful Application of Water to Post-Harvest Biomass Previous work on *Monarda fistulosa* has confirmed that the carvacrol and thymol can convert to thymoquinone in the biomass during the post-harvest drying period. Optimizing post-harvest treatments such as storage in a distillation still, polypropylene bags and windrowing revealed that the degree of conversion was fastest in the windrowed (cutting the plant 4-6 inches above ground and leaving the biomass to dry over the ground in a pile) material, followed by storage in polypropylene bags, and the distillation still.

Figure 3:
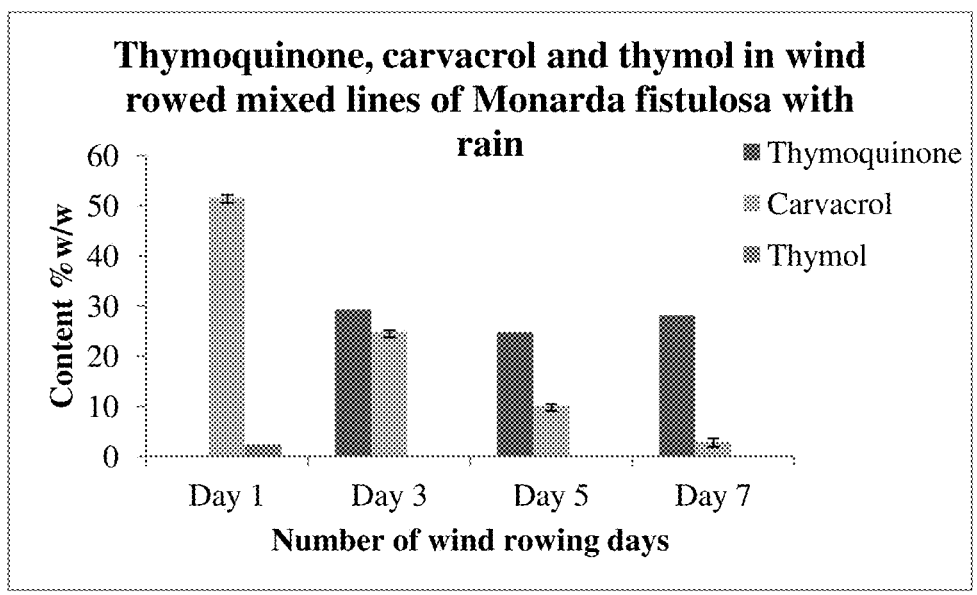
FIG. 3 is a graph of the levels of thymoquinone, carvacrol and thymol in windrowed mixed lines with 2.5 in. of cumulative precipitation on Day 1, and 2 after harvest.
Figure 4:
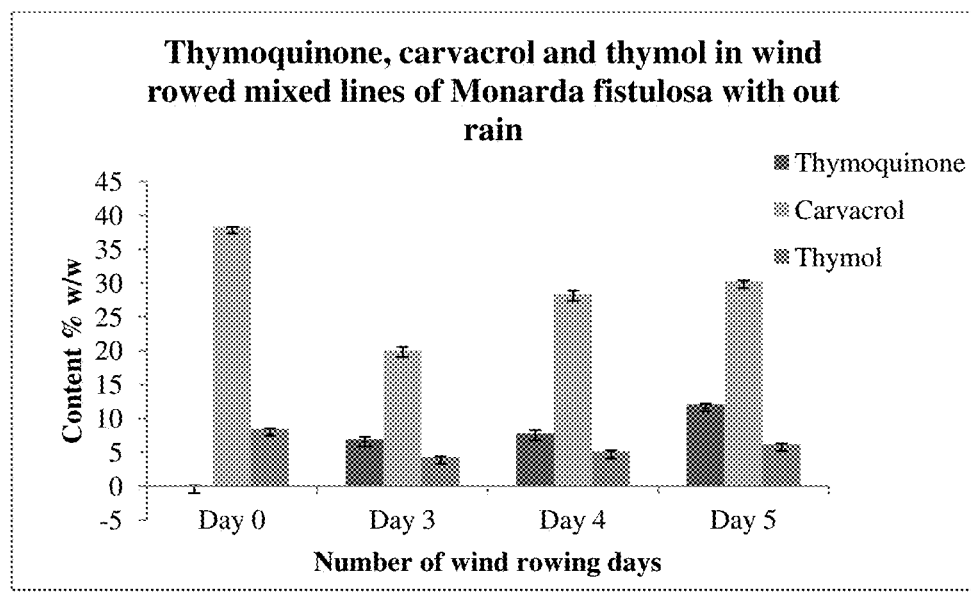
FIG. 4 is a graph of the thymoquinone, carvacrol and thymol levels in windrowed mixed lines with no precipitation.

In the field study, it was observed that the rain was instrumental and also critical for a quicker conversion of carvacrol and thymol to thymoquinone. The thymoquinone level in two harvests done in subsequent weeks, where it had rained on Day 1, and 2 (cumulative 2.5 inch) (FIG. 3) after the first harvest and no rain (FIG. 4) after the second harvest, was remarkably different.

In the second harvest, the conversion to thymoquinone was very slow and the desired levels of thymoquinone were not met during the 5 day drying period seen in the harvest previous week. A high amount of residual carvacrol and thymol was also detected in the dried biomass, indicating that the conversion was not complete.

Figure 5:
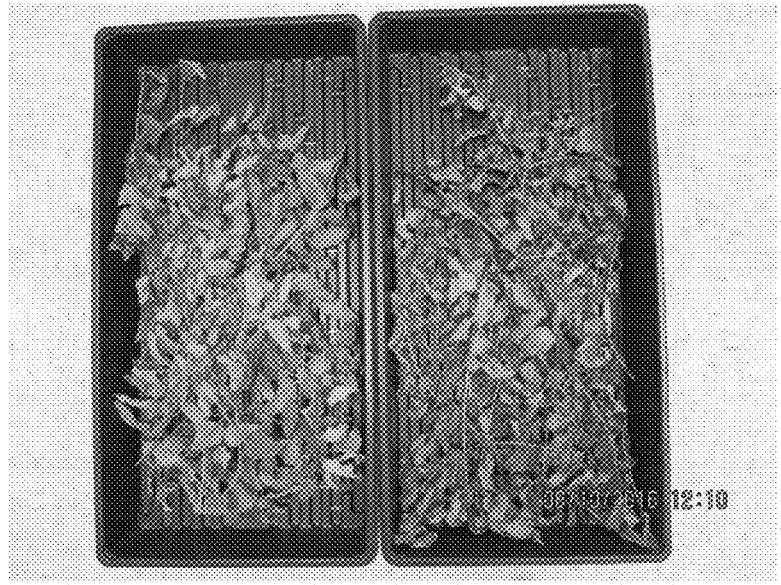
FIG. 5 is a photograph of *Monarda fistulosa* windrowed dry (left tray) and wetted once a day for 4 days (right tray).

This led to the hypothesis that water was allowing the bioconversion of carvacrol and thymol to thymoquinone to happen faster than when no excess water was present on the biomass. To test this concept, a single variable analysis was done with the biomass of a clonal line of *Monarda fistulosa* with high thymol content, growing in the controlled conditions of a greenhouse (FIG. 5).

An equal amount (100 gm) of biomass from *Monarda fistulosa* was stored in two trays with perforated bottom, and one marked as 'wet' was purposefully watered with about 2 liters of water once a day on day 1, 2, 5 and 6 after harvest. The perforated tray did not allow any accumulation of still water and did not submerge the biomass. The control was kept 'dry' and in an adjacent location to expose both trays to similar temperature (21-23° C.) and humidity (45-49%) in the lab over a period of 7 days.

Figure 6:
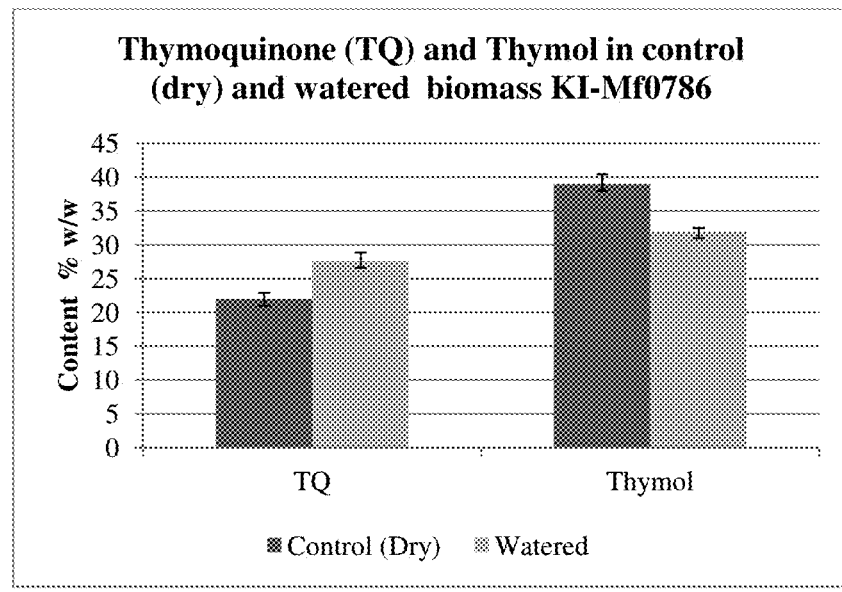
FIG. 6 is a graph of *Monarda fistulosa* oil extracted on day 7 showing a remarkable increase in thymoquinone in the purposefully watered biomass.

Essential oil was extracted from each of this biomass by steam distillation and the oil was tested for content by HPLC. The oil from biomass that was purposefully watered had higher amount of thymoquinone (27.6% wet vs 22.0% dry) (FIG. 6) when tested 7 days after harvest. Thymol was not completely converted and no carvacrol was detected in this oil.

Based on the lab results, a clonal line of *Monarda fistulosa* with high thymol content and whose biomass was available was harvested and windrowed.

Figure 7:
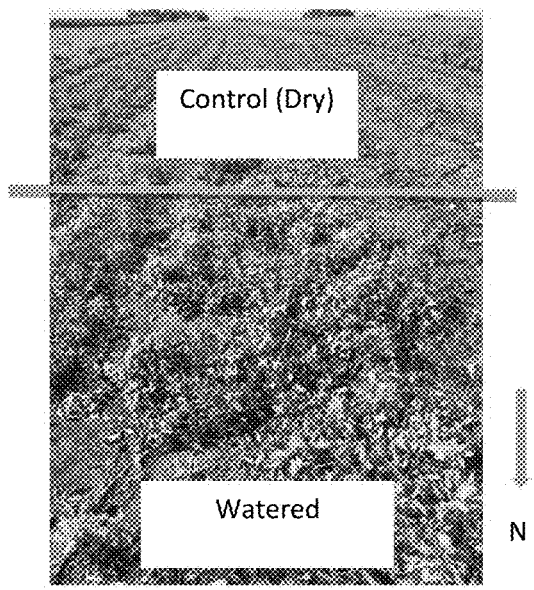
FIG. 7 is a photograph of the windrowed biomass of a clonal line of *Monarda fistulosa*.

The windrow was divided into north and south plot (FIG. 7). The north plot was purposefully watered from a hose attached to a water tanker, on day 1 and 2 after harvest. The control south plot was left dry without additional watering.

The average temperature during this experiment was between 17-27° C. and no rainfall was recorded during the test period.

Samples were taken at Day 0 and Day 3. Essential oil was extracted from each of the biomass by steam distillation and the oil was tested for the content by HPLC.

Figure 8:
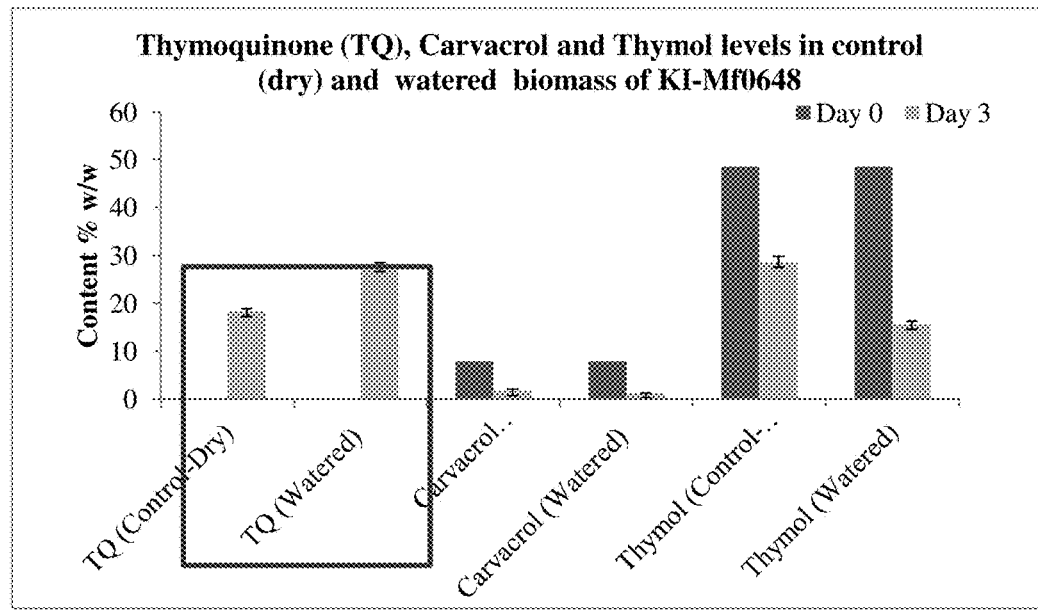
FIG. 8 is a graph of the thymoquinone, carvacrol and thymol levels in control (dry) and watered biomass of a clonal line of *Monarda fistulosa* after 3 days of harvest.

Oil from the biomass that was purposefully watered for 2 days after harvest had significantly higher amount of thymoquinone (27.7% wet vs 18.3% dry) (FIG. 8). There was a remarkable amount of thymol left in the biomass that had potential to convert to thymoquinone.

The experiment could not be continued as a controlled study because on Day 4 after the harvest, both the North and South plot were wet with almost 0.18 in of rain.

Figure 9:
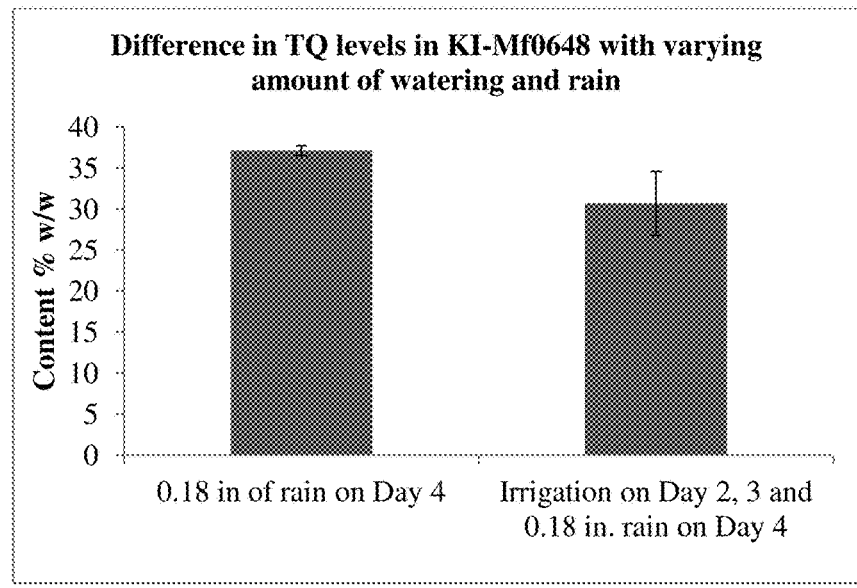
FIG. 9 is a graph of the thymoquinone level in a clonal line of *Monarda fistulosa* with different levels of wetness.
Figure 10:
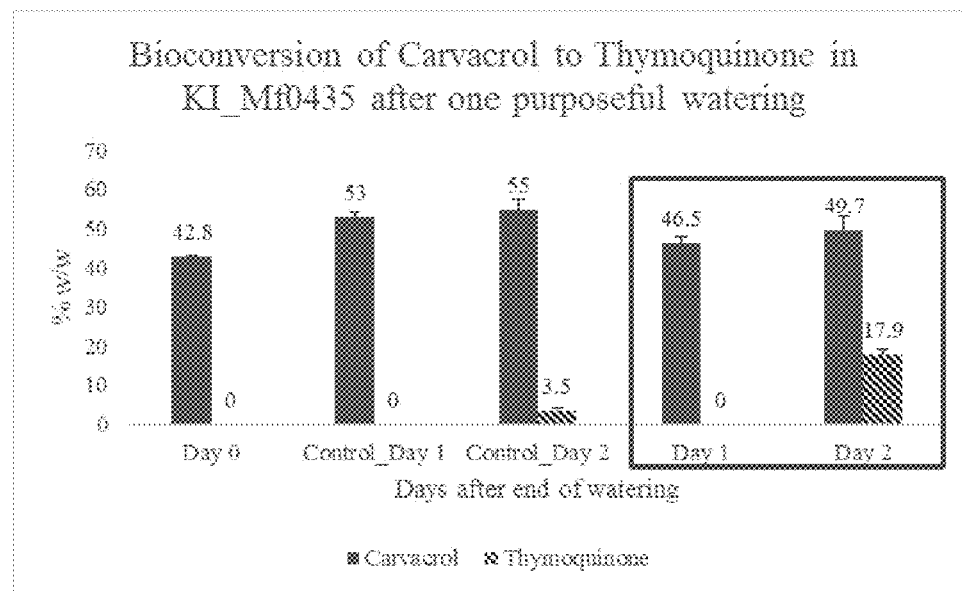
FIG. 10 is a chart of thymoquinone levels in *Monarda fistulosa* biomass watered once after harvest.
Figure 11:
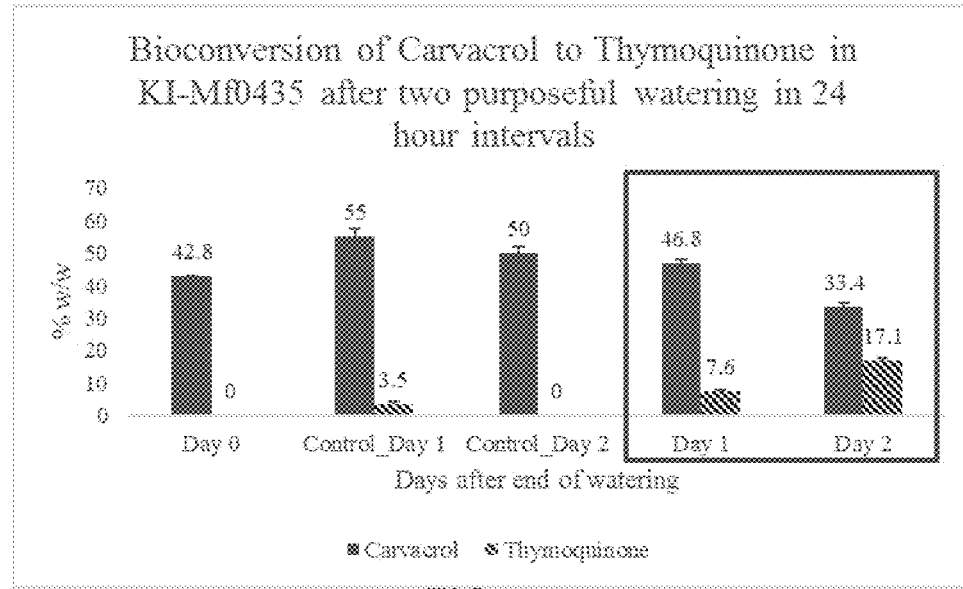
FIG. 11 is a chart of thymoquinone levels in *Monarda fistulosa* biomass watered twice over two 24-hour intervals after harvest.
Figure 12:
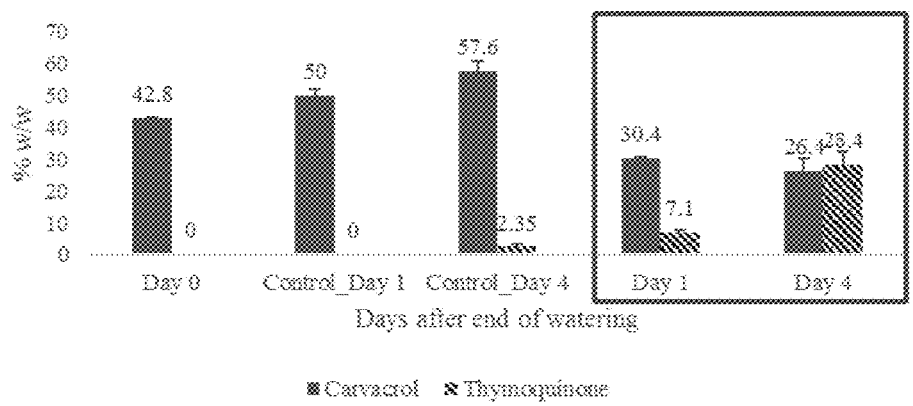
FIG. 12 is a chart of thymoquinone levels in *Monarda fistulosa* biomass watered three times over three 24-hour intervals after harvest.

However, the samples taken on Day 7 after harvest from both the plots showed higher thymoquinone levels (32-37%) (FIG. 9) than Day 3 after harvest. No residual carvacrol or thymol was detected in these oils indicating that the starting material for this bioconversion was no longer available.

The north plot that was purposefully watered showed a slightly lower thymoquinone than the dry plot. It is possible that the thymoquinone may have already been converted completely between Days 4-6 and may have started to evaporate or washed away after conversion.

In conclusion, purposefully watering the windrowed biomass of clonal and/or mixed lines of *Monarda fistulosa* after harvesting positively increases the rate of conversion of carvacrol and thymol to thymoquinone, thus reducing the number of days that the biomass has to be left on the ground.

On an average, 2-3 days of purposeful application of water to post-harvest biomass starting the day after the harvest could allow the maximum conversion, also identified as the time when the residual carvacrol and thymol are at the lowest detected levels in the steam distilled oil.

There is also indication that after complete conversion has happened, thymoquinone may start to evaporate, and hence the day of oil extraction should be optimized based on maximum conversion and conservation of thymoquinone.

Example 4-Bioconversion of Carvacrol to Thymoquinone in High-Carvacrol Accumulating Selected Clonal Lines of *Monarda fistulosa*

The purpose was to determine the effect of frequency of watering at 24-hour interval on the rate of conversion of carvacrol/thymol to thymoquinone within a 7-day period
Materials and Methods A controlled single variable study was designed to treat biomass with watering at 24-hour intervals for 1, 2, 3 and 4 times.

Figure 13:
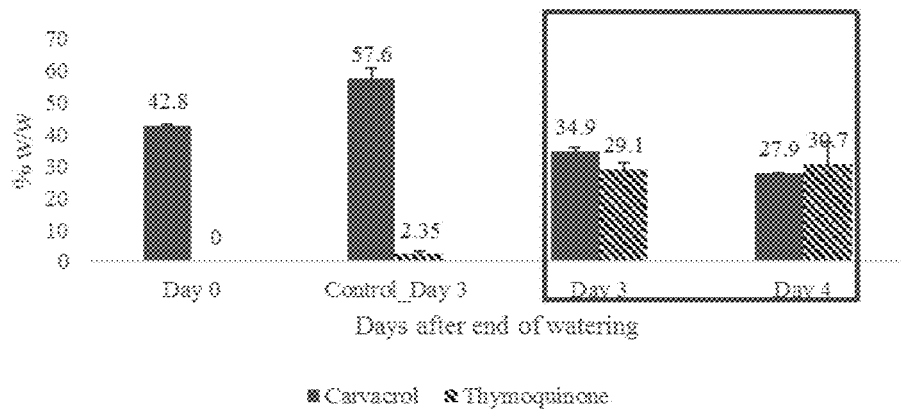
FIG. 13 is a chart of thymoquinone levels in *Monarda fistulosa* biomass watered four times over four 24-hour intervals after harvest.

The *monarda* clonal line KI-Mf0435 was cut and a windrow was created by stacking cut biomass in a perforated tray, 2 inches tall. One tray each was subjected for 1, 2, 3 and 4 days of purposeful watering (5 L per 650 gm of starting material). The control was kept dry for each 24-hour interval treatment. The essential oil was extracted after 24 and 48 hours of each treatment, and from the dry control for each day.
Results The control that was kept dry did not show conversion or formation of thymoquinone until 7 days after the harvest (FIGS. 10, 11, 12 and 13). The biomass samples that were watered started formation of detectable thymoquinone within 24-48 hours after watering was complete (FIGS. 10-13). Thirty percent (30%) of thymoquinone was obtained within 7 days of harvest with a frequency of four waterings in a 24-hour interval followed by a two-day drying period. (FIG. 13).
Discussion and Conclusion This data strongly indicates that purposeful watering at intervals of 24 hours initiates as well as increases the rate of conversion of carvacrol to thymoquinone. A high amount of the starting molecule was detected even at the end of Day 7, hence there is further possibility for the TQ to increase more than 30%

Based on this study, the following study was designed with a frequency of three watering application in 24-hour intervals.

Example 5—Effect of Temperature and Light on the Bioconversion of Carvacrol to Thymoquinone in High-Carvacrol Accumulating Selected Clonal Lines of *Monarda fistulosa*

The purpose of this study was to determine the effect of temperature and light on the conversion of carvacrol/thymol and formation of thymoquinone in biomass watered for three times in 24-hour intervals.

Materials and Methods

A controlled 13-day single variable study was designed to treat biomass with three watering at 24 hour intervals, and stored at two temperatures, and in either a lighted or a darkened area.

Harvested biomass of a *monarda* clonal line was mixed to assist uniform sampling and divided into six trays (three sample trays and three control trays), with each tray having 650 gm of wilted material. The first set of sample and control trays (Lot A) were maintained at 20-22° C. and at humidity between 43-48%. The second set of sample and control trays (Lot B) were maintained at 30-32° C. The third set of sample and control trays (Lot C) were maintained in the dark at 20-22° C. The control trays were kept dry all the time. Each of the three sample trays containing 650 gm biomass were watered with 5 L water three times at a 24-hour interval, starting on the day after the harvest, followed by a drying period.

Figure 14:
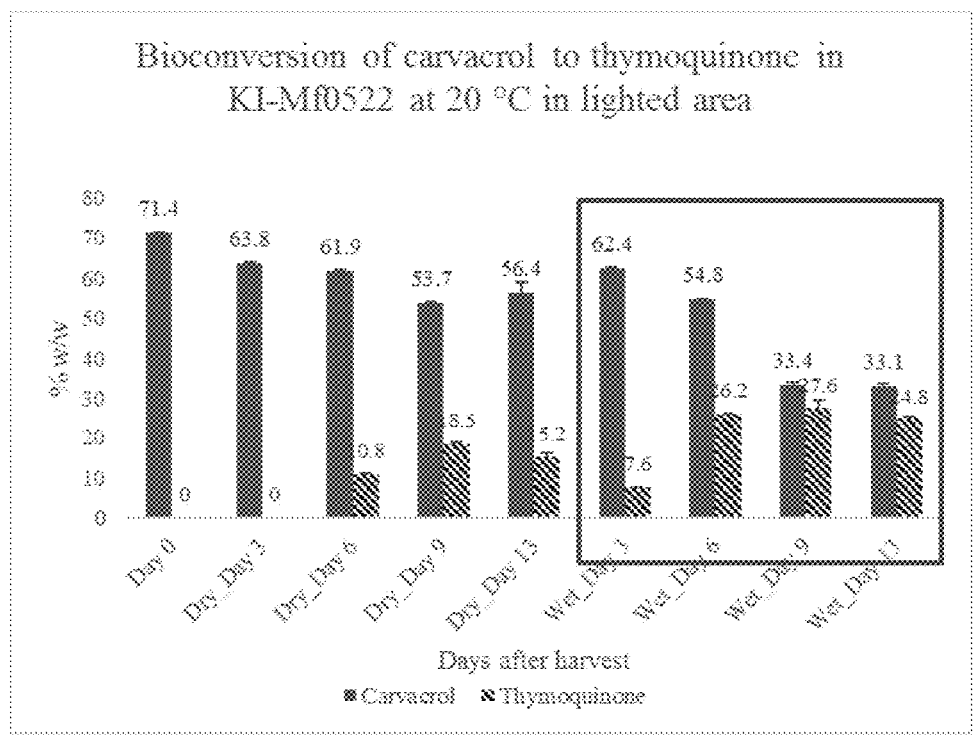
FIG. 14 is a chart of thymoquinone levels in *Monarda fistulosa* biomass kept at 20-22° C. in a lighted area after harvest.

Samples were collected on Day 3, 6, 9 and 13 from all locations. Essential oil from each sample and control was extracted using steam distillation. Essential oil was analyzed for the content of carvacrol, thymol and thymoquinone using the previously established HPLC method
Results Lot A samples kept in the lighted area dried well and showed depletion of carvacrol and the formation of thymoquinone starting from Day 3. (FIG. 14). The highest thymoquinone level was noted between Day 6 and Day 9 followed by a slight decline on Day 13. The residual carvacrol was detected even on Day 13, indicating that more than 24.8% thymoquinone could be accumulated in oil from this selected line. In contrast, the conversion in the control dry sample was very slow, with only 15.2% thymoquinone obtained after 13 days.

Figure 15:
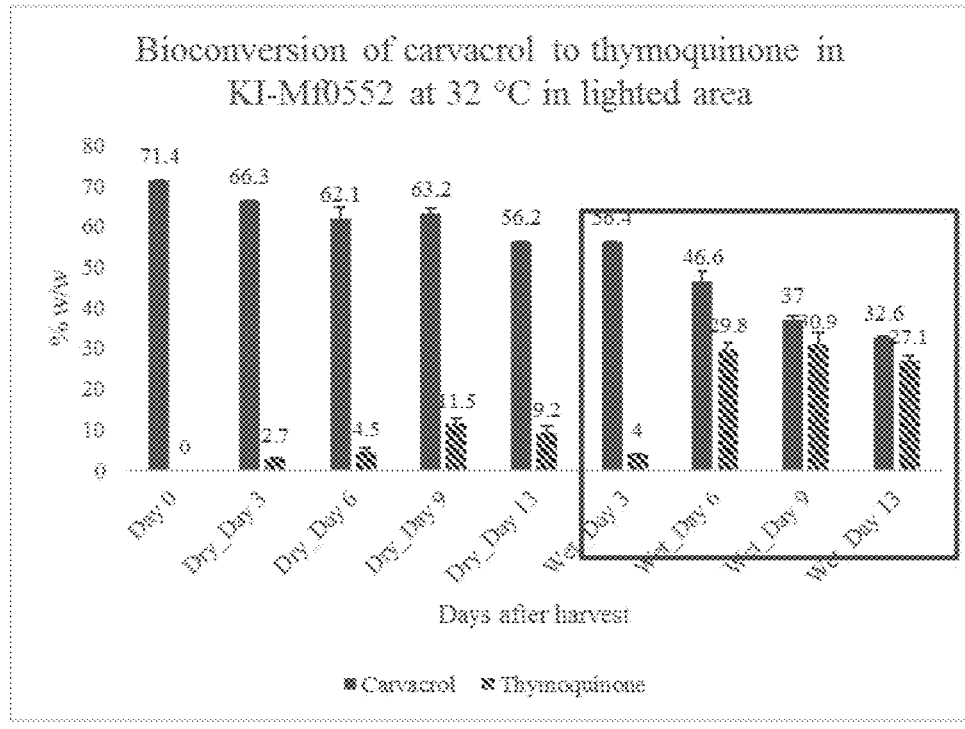
FIG. 15 is a chart of thymoquinone levels in *Monarda fistulosa* biomass kept at 30-32° C. in a lighted area after harvest.

Lot B samples kept at elevated temperature and lighted area dried well and converted marginally higher thymoquinone than the 20° C. sample. (FIG. 15). In contrast, the control dry sample converted very little thymoquinone with more than 50% carvacrol still detectable, indicating that dry and high temperature was highly unfavorable for the bioconversion. The difference in TQ formation (>30%) and the depletion of carvacrol between control and wet samples was significant on all days. The highest TQ was observed on Day 6 and Day 9 followed by a slight decline on Day 13.

Figure 16:
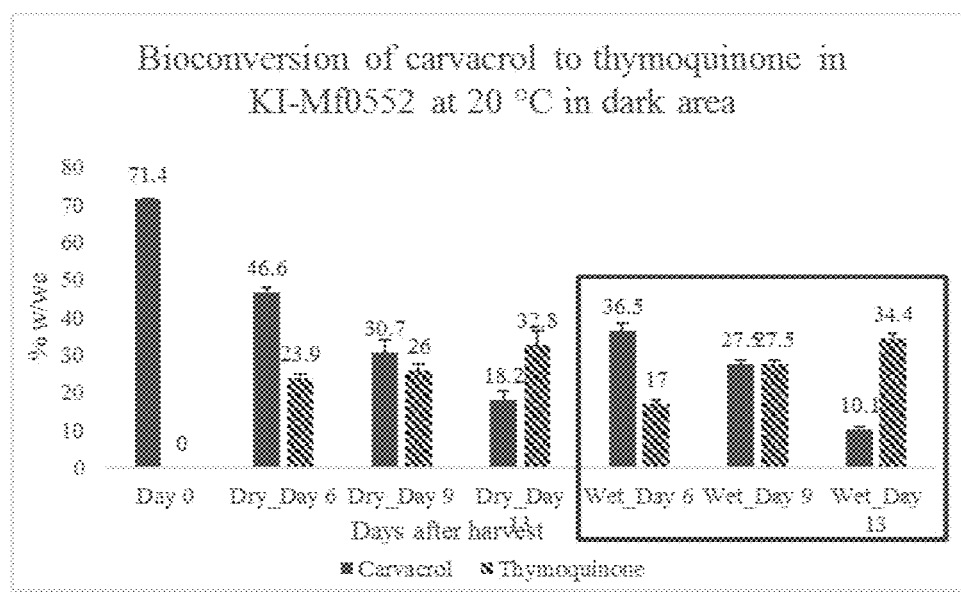
FIG. 16 is a chart of thymoquinone levels in *Monarda fistulosa* biomass kept at 20° C. in a darkened area after harvest.

Lot C samples kept in dark did not become crispy dry like all other samples. The control was pliable and greenish in color when compared to the biomass kept in lighted areas. The wet sample had soggy leaves and all samples had a strong musty odor. The oil from both control and sample had the highest TQ at >30% level (FIG. 16), with relatively lower yield than other sources and with a noticeable musty note in the odor profile. The control showed efficient and similar conversion to thymoquinone indicating that light is not critical in this bioconversion process. In the 13-day study period, the formation of thymoquinone showed an upward trend in both control and wet sample, with no decline observed. The highest depletion of carvacrol was seen in the wet sample after 13 days, indicating that the wetness and lack of light were favorable for such conversion.
Discussion and Conclusion No thymol was detected in any of the oils from the clonal line.

A minimum frequency of 3 purposeful watering was needed to initiate and promote the bioconversion of carvacrol to thymoquinone in these selected lines. Three days of watering can convert up to 55% of carvacrol in 13 days to thymoquinone under lighted conditions, and up to 85% in dark and humid conditions. The complete conversion of carvacrol to thymoquinone needed more than 13 days.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A method of producing thymoquinone, comprising the steps of:
   (a) cultivating plants of *Monarda fistulosa* either by planting seed or by transplanting cuttings;
   (b) growing said plants of *Monarda fistulosa* until elevated levels of carvacrol and/or thymol are present in the plants;
   (c) cutting said plants;
   (d) allowing material of said cut plants to senesce in the presence of oxygen for a period of greater than one day and less than 14 days to induce conversion of carvacrol and/or thymol to thymoquinone; and
   (e) collecting thymoquinone from said senesced material.

2. The method of claim 1, wherein allowing senescence increases the level of thymoquinone to between 10% and 40%.

3. The method of claim 1, wherein water is purposely applied to the material at least once over said period of senescence.

4. The method of claim 3, wherein water is applied by a method selected from the group consisting of irrigation and spraying either by hand or mechanical application.

5. A method of producing thymoquinone, comprising the steps of:
   (a) cultivating plants of *Monarda fistulosa* either by planting seed or by transplanting cuttings;
   (b) growing said plants of *Monarda fistulosa* until elevated levels of carvacrol and/or thymol are present in the plants;
   (c) cutting said plants;
   (d) applying water to material of said cut plants for a period of greater than one day and less than 14 days to induce conversion of carvacrol and/or thymol to thymoquinone; and
   (e) collecting thymoquinone from said material.

6. The method of claim 5, wherein the application of water increases the level of thymoquinone to between 10% and 40%.

* * * * *